United States Patent
Ichim et al.

(10) Patent No.: US 11,957,727 B2
(45) Date of Patent: *Apr. 16, 2024

(54) PREVENTION OF NEUROINFLAMMATION ASSOCIATED MEMORY LOSS USING NUTRACEUTICAL COMPOSITIONS

(71) Applicant: Therapeutic Solutions International, Inc., Oceanside, CA (US)

(72) Inventors: Thomas E. Ichim, Oceanside, CA (US); Famela Ramos, Oceanside, CA (US); James Veltmeyer, Oceanside, CA (US); Timothy G. Dixon, Oceanside, CA (US)

(73) Assignee: Therapeutic Solutions International, Inc, Oceanside, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/395,249

(22) Filed: Aug. 5, 2021

(65) Prior Publication Data
US 2022/0040248 A1 Feb. 10, 2022

Related U.S. Application Data

(60) Provisional application No. 63/061,202, filed on Aug. 5, 2020.

(51) Int. Cl.
| | | |
|---|---|---|
| *A61K 36/82* | (2006.01) |
| *A61K 31/09* | (2006.01) |
| *A61K 31/122* | (2006.01) |
| *A61K 31/26* | (2006.01) |
| *A61K 31/353* | (2006.01) |
| *A61K 36/31* | (2006.01) |
| *A61K 36/45* | (2006.01) |
| *A61K 36/71* | (2006.01) |
| *A61P 25/28* | (2006.01) |

(52) U.S. Cl.
CPC .............. *A61K 36/82* (2013.01); *A61K 31/09* (2013.01); *A61K 31/122* (2013.01); *A61K 31/26* (2013.01); *A61K 31/353* (2013.01); *A61K 36/31* (2013.01); *A61K 36/45* (2013.01); *A61K 36/71* (2013.01); *A61P 25/28* (2018.01)

(58) Field of Classification Search
CPC ........ A61K 31/65; A61K 36/31; A61K 36/45; A61K 36/71; A61K 36/82; A61P 25/28
See application file for complete search history.

(56) References Cited

U.S. PATENT DOCUMENTS 11,229,674 B1 * 1/2022 Ichim ..................... A61P 29/00

OTHER PUBLICATIONS

Ordonez AA, et al "Sulforaphane Exhibits Antiviral Activity Against Pandemic SARS-COV-2 and Seasonal HCoV-OC43 Coronaviruses in vitro </i>and in Mice" Nature: Commun Biol</i>, Mar. 18, 2022, 5:242, 11 pages; doi:10.1038/s42003-022-03189-z (Year: 2022).*

* cited by examiner

*Primary Examiner* — Aaron J Kosar
(74) *Attorney, Agent, or Firm* — Baumgartner PatentLaw, LLC; Marc Baumgartner

(57) ABSTRACT

Disclosed are means, methods, and therapeutic compositions for prevention of memory loss during situations of neuroinflammation. In one embodiment the invention teaches administration of the therapeutic combination of ingredients comprising of pterostilbene, *Nigella sativa*, sulforaphane, and epigallocatechin-3-gallate (EGCG) to a mammal suffering from inflammation in order to preserver memory function.

10 Claims, 2 Drawing Sheets

Mice administered saline, LPS, LPS + QuadraMune (1) and LPS + QuadraMune (2). Sacrificed at indicatedtimes. Brain tissue homogenated assessed for IL-6 cytokine production. Quantified using ELISA.

PREVENTION OF NEUROINFLAMMATION ASSOCIATED MEMORY LOSS USING NUTRACEUTICAL COMPOSITIONS

CROSS-REFERENCE TO RELATED APPLICATIONS

This application claims priority to U.S. Provisional Application No. 63/061,202, filed Aug. 5, 2020, which is incorporated herein by reference in its entirety.

FIELD OF THE INVENTION

The invention relates to the field of treating neuroinflammation associated memory loss through the use of therapeutic compositions, such as nutraceuticals.

BACKGROUND

Neuroinflammation has been associated with numerous examples of memory inhibition and/or memory loss. It has been observed that anxiety and memory are two closely related paradigms. Anatomically, brain structures such as hippocampus/amygdala are implicated both in anxiety and memory. Anxiety, depression and calming effect are interrelated functions in the brain. For example, administration of THC (Tetrahydrocannabinol) in animals impaired the memory and simultaneously found to increase the symptoms of anxiety. Similar type of effect was found to occur in humans during acute administration of cannabinoids. There are reports that various monoamines (catecholamines) can interfere with memory enhancement and anxiety. Increase in brain serotonergic transmission can interfere with memory and learning acquisition. The role of 5-HT in anxiety is very clearly established. Increase in brain 5-HT levels leads to anxiety while decrease in brain 5-HT levels leads to anti-anxiety.

SUMMARY

The teachings herein relate to methods of inhibiting inflammation associated memory dysfunction comprising administering to a patient in need of treatment a composition containing one or more of the following ingredients: a) Green Tea and/or extract thereof; b) Blueberry and/or extract thereof; c) Nigella sativa and/or extract thereof; and d) broccoli and/or extract thereof.

Preferred embodiments include methods wherein said green tea extract is epigallocatechin-3-gallate or an analogue thereof.

Preferred embodiments include methods wherein said blueberry extract is pterostilbene or an analogue thereof.

Preferred embodiments include methods wherein said Nigella sativa extract is thymoquinone or an analogue thereof.

Preferred embodiments include methods wherein said broccoli extract is sulforaphane or an analogue thereof.

Preferred embodiments include methods wherein said therapeutic combination is administered at a dosage and frequency sufficient to inhibit neural inflammation.

Preferred embodiments include methods wherein said neural inflammation is microglial activation.

Preferred embodiments include methods wherein said microglial activation is upregulation of HLA II on microglia.

Preferred embodiments include methods wherein said microglial activation is upregulation of IL-10 production from microglia.

Preferred embodiments include methods wherein said microglial activation is upregulation of CD40.

Preferred embodiments include methods wherein said microglial activation is upregulation of CD80.

Preferred embodiments include methods wherein said microglial activation is upregulation of CD86.

Preferred embodiments include methods wherein said microglial activation is upregulation of nitric oxide production.

Preferred embodiments include methods wherein said inflammation associated memory dysfunction is caused by enhanced production of indolamine 2,3 deoxygenase metabolites.

Preferred embodiments include methods wherein said indolamine 2,3 deoxygenase metabolites are quinilonic acid and kyneurinin.

DETAILED DESCRIPTION OF THE INVENTION

Figure 1:
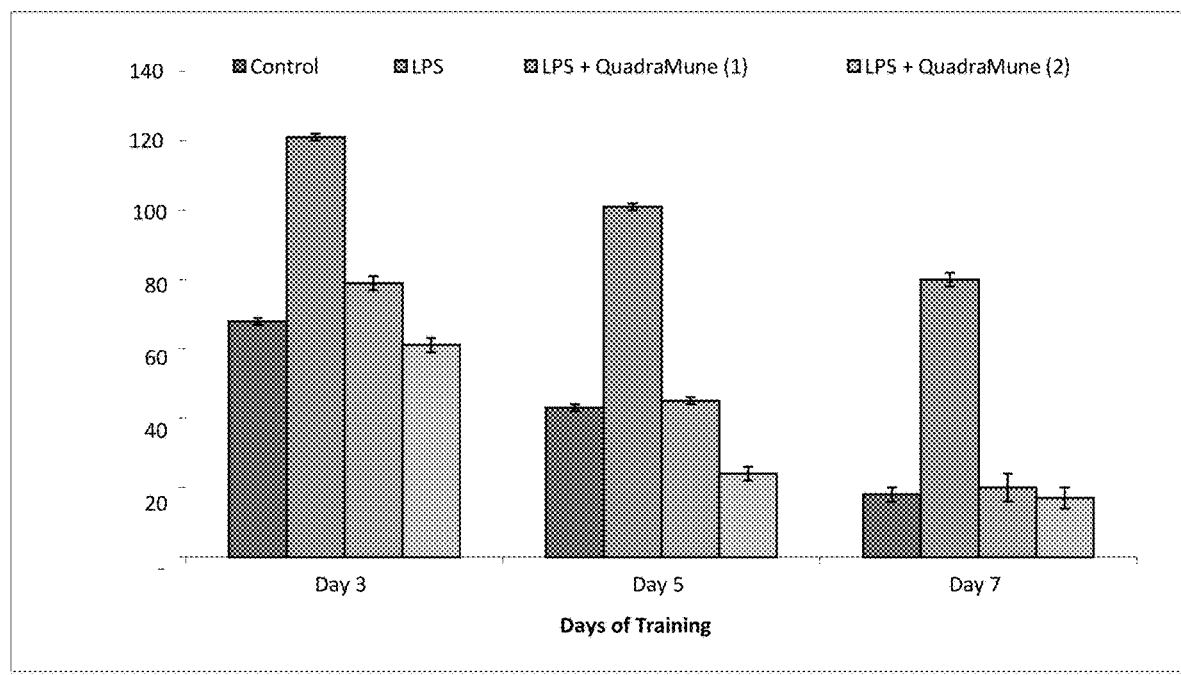
FIG. 1 is a bar graph showing pretreatment with the product containing a) epigallocatechin-3-gallate b) thymoquinone, c) sulforaphane, and d) pterostilbene sold under the trademark QUADRAMUNE® preserved memory in mice.

The invention provides the use of pterostilbene alone, in liposomal formulations, and in nutraceutical compositions.
Pterostilbene Pterostilbene (trans-3,5-dimethoxy-4-hydroxystilbene) is a natural polyphenolic compound, primarily found in fruits, such as blueberries, grapes, and tree wood. It has been demonstrated to possess potent antioxidant and anti-inflammatory properties. It is a dimethylated analog of resveratrol which is found in blueberries [1], and is believed to be one of the active ingredients in ancient Indian Medicine [2]. The pterostilbene molecule is structurally similar to resveratrol, the antioxidant found in red wine that has comparable anti-inflammatory, and anticarcinogenic properties; however, pterostilbene exhibits increased bioavailability due to the presence of two methoxy groups which cause it to exhibit increased lipophilic and oral absorption [3-7]. In animal studies, pterostilbene was shown to have 80% bioavailability compared to 20% for resveratrol making it potentially advantageous as a therapeutic agent [3].

We have demonstrated the pterostilbene administered in the form of nanostilbene in cancer patients results in increased NK cell activity, as well as interferon gamma production. Additionally, pterostilbene has shown to inhibit inflammatory cytokines associated with ARDS. For example, studies have demonstrated inhibition of interleukin-1 [8], interleukin-6 [9, 10], interleukin-8 [11], and TNF-alpha [12], by pterostilbene.

COVID-19 has been associated with endothelial activation and coagulopathy. It is interesting to note that numerous studies have demonstrated endothelial protective effects of pterostilbene. For example, Zhang et al. investigated the anti-apoptotic effects of pterostilbene in vitro and in vivo in mice. Exposure of human umbilical vein VECs (HUVECs) to oxLDL (200 µg/ml) induced cell shrinkage, chromatin condensation, nuclear fragmentation, and cell apoptosis, but pterostilbene protected against such injuries. In addition, PT injection strongly decreased the number of TUNEL-positive cells in the endothelium of atherosclerotic plaque from apoE(−/−) mice. OxLDL increased reactive oxygen species (ROS) levels, NF-κB activation, p53 accumulation, apoptotic protein levels and caspases-9 and -3 activities and decreased mitochondrial membrane potential (MMP) and cytochrome c release in HUVECs. These alterations were attenuated by pretreatment. Pterostilbene inhibited the expression of lectin-like oxLDL receptor-1 (LOX-1) expression in vitro and in vivo. Cotreatment with PT and siRNA of LOX-1 synergistically reduced oxLDL-induced apoptosis in HUVECs. Overexpression of LOX-1 attenuated the protection by pterostilbene and suppressed the effects of pterostilbene on oxLDL-induced oxidative stress. Pterostilbene may protect HUVECs against oxLDL-induced apoptosis by downregulating LOX-1-mediated activation through a pathway involving oxidative stress, p53, mitochondria, cytochrome c and caspase protease [13]. Endothelial protection by pterostilbene [14, 15], and its analogue resveratrol are well known [16, 17].

Kalonji

First. Taking Kalonji increases the potency of the immune system [18, 19]. Specifically, it has been shown that kalonji activates the natural killer cells of the immune system. Natural killer cells, also called NK cells are the body's first line of protection against viruses. It is well known that patients who have low levels of NK cells are very susceptible to viral infections. Kalonji has been demonstrated to increase NK cell activity. In a study published by Dr. Majdalawieh from the American University of Sharjah, Sharjah, United Arab Emirates [20], it was shown that the aqueous extract of *Nigella sativa* significantly enhances NK cytotoxic activity. According to the authors, this supports the idea that NK cell activation by Kalonji can protect not only against viruses, but may also explain why some people report this herb has activity against cancer. It is known that NK cells kill virus infected cells but also kill cancer cells. There are several publications that show that Kalonji has effects against cancer [21-35].

Second. Kalonji suppresses viruses from multiplying. If the virus manages to sneak past the immune system and enters the body, studies have shown that Kalonji, and its active ingredients such as thymoquinone, are able to directly stop viruses, such as coronaviruses and others from multiplying. For example, a study published from University of Gaziantep, in Turkey demonstrated that administration of Kalonji extract to cells infected with coronavirus resulted in suppression of coronavirus multiplication and reduction of pathological protein production [36]. Antiviral activity of Kalonji was demonstrated in other studies, for example, for example, viral hepatitis, and others [37].

Third. Kalonji protects the lungs from pathology. Kalonji was also reported by scholars to possess potent anti-inflammatory effects where its active ingredient thymoquinone suppressed effectively the lipopolysaccharide-induced inflammatory reactions and reduced significantly the concentration of nitric oxide, a marker of inflammation [38]. Moreover, Kalonji has been proven to suppress the pathological processes through blocking the activities of IL-1, IL-6, nuclear factor-KB [39], IL-1 β, cyclooxygenase-1, prostaglandin-E2, prostaglandin-D2 [40], cyclooxygenase-2, and TNF-α [41] that act as potent inflammatory mediators and were reported to play a major role in the pathogenesis of Coronavirus infection.

Fourth. Kalonji protects against sepsis/too much inflammation. In peer reviewed study from King Saud University, Riyadh, Saudi Arabia, scientists examined two sets of mice (n=12 per group), with parallel control groups, were acutely treated with thymoquinone (ingredient from Kalonji) intraperitoneal injections of 1.0 and 2.0 mg/kg body weight, and were subsequently challenged with endotoxin Gram-negative bacteria (LPS 0111:B4). In another set of experiments, thymoquinone was administered at doses of 0.75 and 1.0 mg/kg/day for three consecutive days prior to sepsis induction with live *Escherichia coli*. Survival of various groups was computed, and renal, hepatic and sepsis markers were quantified. Thymoquinone reduced mortality by 80-90% and improved both renal and hepatic biomarker profiles. The concentrations of IL-la with 0.75 mg/kg thymoquinone dose was 310.8±70.93 and 428.3±71.32 pg/ml in the 1 mg/kg group as opposed to controls (1187.0±278.64 pg/ml; P<0.05). Likewise, IL-10 levels decreased significantly with 0.75 mg/kg thymoquinone treatment compared to controls (2885.0±553.98 vs. 5505.2±333.96 pg/ml; P<0.01). Mice treated with thymoquinone also exhibited relatively lower levels of TNF-α and IL-2 (P values=0.1817 and 0.0851, respectively). This study gives strength to the potential clinical relevance of thymoquinone in sepsis-related morbidity and mortality reduction and suggests that human studies should be performed [42].

Sulforaphane

Sulforaphane [1-isothiocyanato-4-(methylsulfinyl)-butane], an isothiocyanate, is a chemopreventive photochemical which is a potent inducer of phase II enzyme involved in the detoxification of xenobiotics [43]. Sulforaphane is produced from the hydrolysis of glucoraphanin, the most abundant glucosinolate found in broccoli, and also present in other Brassicaceae [44]. Numerous studies have reported prevention of cancer [45-49], as well as cancer inhibitory properties of sulforaphane [50-55]. Importantly, this led to studies which demonstrated anti-inflammatory effects of this compound.

One of the fundamental features of inflammation is production of TNF-alpha from monocytic lineage cells. Numerous studies have shown that sulforaphane is capable of suppressing this fundamental initiator of inflammation, in part through blocking NF-kappa B translocation. For example, Lin et al. compared the anti-inflammatory effect of sulforaphane on LPS-stimulated inflammation in primary peritoneal macrophages derived from Nrf2 (+/+) and Nrf2 (−/−) mice. Pretreatment with sulforaphane in Nrf2 (+/+) primary peritoneal macrophages potently inhibited LPS-stimulated mRNA expression, protein expression and production of TNF-alpha, IL-1beta, COX-2 and iNOS. HO-1 expression was significantly augmented in LPS-stimulated Nrf2 (+/+) primary peritoneal macrophages by sulforaphane. Interestingly, the anti-inflammatory effect was attenuated in Nrf2 (−/−) primary peritoneal macrophages. We concluded that SFN exerts its anti-inflammatory activity mainly via activation of Nrf2 in mouse peritoneal macrophages [56]. In a similar study, LPS-challenged macrophages were observed for cytokine production with or without sulforaphane pretreatment. Macrophages were pre-incubated for 6 h with a wide range of concentrations of SFN (0 to 50 µM), and then treated with LPS for 24 h. Nitric oxide (NO) concentration and gene expression of different inflammatory mediators, i.e., interleukin (IL)-6, tumor necrosis factor (TNF)-α, and IL-1β, were measured. sulforaphane neither directly reacted with cytokines, nor with NO. To understand the mechanisms, the authors performed analyses of the expression of regulatory enzyme inducible nitric oxide synthase (iNOS), the transcription factor NF-E2-related factor 2 (Nrf2), and its enzyme heme-oxygenase (HO)-1. The results revealed that LPS increased significantly the expression of inflammatory cytokines and concentration of NO in non-treated cells. sulforaphane was able to prevent the expression of NO and cytokines through regulating inflammatory enzyme iNOS and activation of Nrf2/HO-1 signal transduction pathway [57]. These data are significant because studies have shown both TNF-alpha but also interleukin-6 are involved in pathology of COVID-19 [58-68]. The utilization of sulforaphane as a substitute for anti-IL-6 antibodies would be more economical and potentially without associated toxicity. Other studies have also demonstrated ability of sulforaphane to suppress IL-6 [69-71]. Interestingly, a clinical study was performed in 40 healthy overweight subjects (ClinicalTrials.gov ID NCT 03390855). Treatment phase consisted on the consumption of broccoli sprouts (30 g/day) during 10 weeks and the follow-up phase of 10 weeks of normal diet without consumption of these broccoli sprouts. Anthropometric parameters as body fat mass, body weight, and BMI were determined. Inflammation status was assessed by measuring levels of TNF-α, IL-6, IL-1β and C-reactive protein. IL-6 levels significantly decreased (mean values from 4.76 pg/mL to 2.11 pg/mL with 70 days of broccoli consumption, p<0.001) and during control phase the inflammatory levels were maintained at low grade (mean values from 1.20 pg/mL to 2.66 pg/mL, p<0.001). C-reactive protein significantly decreased as well [72].

An additional potential benefit of sulforaphane is its ability to protect lungs against damage. It is known that the major cause of lethality associated with COVID-19 is acute respiratory distress syndrome (ARDS). It was demonstrated that sulforaphane is effective in the endotoxin model of this condition. In one experiments, BALB/c mice were treated with sulforaphane (50 mg/kg) and 3 days later, ARDS was induced by the administration of LPS (5 mg/kg). The results revealed that sulforaphane significantly decreased lactate dehydrogenase (LDH) activity (as shown by LDH assay), the wet-to-dry ratio of the lungs and the serum levels of interleukin-6 (IL-6) and tumor necrosis factor-α (TNF-α) (measured by ELISA), as well as nuclear factor-KB protein expression in mice with LPS-induced ARDS. Moreover, treatment with sulforaphane significantly inhibited prostaglandin E2 (PGE2) production, and cyclooxygenase-2 (COX-2), matrix metalloproteinase-9 (MMP-9) protein expression (as shown by western blot analysis), as well as inducible nitric oxide synthase (iNOS) activity in mice with LPS-induced ALI. Lastly, the researchers reported pretreatment with sulforaphane activated the nuclear factor-E2-related factor 2 (Nrf2)/antioxidant response element (ARE) pathway in the mice with LPS-induced ARDS [73].

Epigallocatechin-3-gallate (EGCG)

EGCG is similar to sulforaphane in that it has been reported to possess cancer preventative properties. This compound has been shown to be one of the top therapeutic ingredients in green tea. It is known from epidemiologic studies that green tea consumption associates with chemoprotective effects against cancer [74-84]. In addition, similarly to sulforaphane, EGCG has been shown to inhibit inflammatory mediators. The first suggestion of this were studies shown suppression of the pro-inflammatory transcription factor NF-kappa B. In a detailed molecular study, EGCG, a potent antitumor agent with anti-inflammatory and antioxidant properties was shown to inhibit nitric oxide (NO) generation as a marker of activated macrophages. Inhibition of NO production was observed when cells were cotreated with EGCG and LPS. iNOS activity in soluble extracts of lipopolysaccharide-activated macrophages treated with EGCG (5 and 10 microM) for 6-24 hr was significantly lower than that in macrophages without EGCG treatment. Western blot, reverse transcription-polymerase chain reaction, and Northern blot analyses demonstrated that significantly reduced 130-kDa protein and 4.5-kb mRNA levels of iNOS were expressed in lipopolysaccharide-activated macrophages with EGCG compared with those without EGCG. Electrophoretic mobility shift assay indicated that EGCG blocked the activation of nuclear factor-kappaB, a transcription factor necessary for iNOS induction. EGCG also blocked disappearance of inhibitor kappaB from cytosolic fraction. These results suggest that EGCG decreases the activity and protein levels of iNOS by reducing the expression of iNOS mRNA and the reduction could occur through prevention of the binding of nuclear factor-kappaB to the iNOS promoter [85]. Another study supporting ability of EGCG to suppress NF-kappa B examined a model of atherosclerosis in which exposure of macrophage foam cells to TNF-α results in a downregulation of ABCA1 and a decrease in cholesterol efflux to apoA1, which is attenuated by pretreatment with EGCG. Moreover, rather than activating the Liver X receptor (LXR) pathway, inhibition of the TNF-α-induced nuclear factor-κB (NF-κB) activity is detected with EGCG treatment in cells. In order to inhibit the NF-κB activity, EGCG can promote the dissociation of the nuclear factor E2-related factor 2 (Nrf2)-Kelch-like ECH-associated protein 1 (Keap1) complex; when the released Nrf2 translocates to the nucleus and activates the transcription of genes containing an ARE element inhibition of NF-κB occurs and Keap1 is separated from the complex to directly interact with IKKβ and thus represses NF-κB function [86].

The anti-inflammatory effects of EGCG can be seen in the ability of this compound to potently inhibit IL-6, the COVID-19 associated cytokine, in a variety of inflammatory settings. For example, in a cardiac infarct model, rats were subjected to myocardial ischemia (30 min) and reperfusion (up to 2 h). Rats were treated with EGCG (10 mg/kg intravenously) or with vehicle at the end of the ischemia period followed by a continuous infusion (EGCG 10 mg/kg/h) during the reperfusion period. In vehicle-treated rats, extensive myocardial injury was associated with tissue neutrophil infiltration as evaluated by myeloperoxidase activity, and elevated levels of plasma creatine phosphokinase. Vehicle-treated rats also demonstrated increased plasma levels of interleukin-6. These events were associated with cytosol degradation of inhibitor kappaB-alpha, activation of IkappaB kinase, phosphorylation of c-Jun, and subsequent activation of nuclear factor-kappaB and activator protein-1 in the infarcted heart. In vivo treatment with EGCG reduced myocardial damage and myeloperoxidase activity. Plasma IL-6 and creatine phosphokinase levels were decreased after EGCG administration. This beneficial effect of EGCG was associated with reduction of nuclear factor-kB and activator protein-1 DNA binding [87]. In an inflammatory model of ulcerative colitis (UC) mice were randomly divided into four groups: Normal control, model (MD), 50 mg/kg/day EGCG treatment and 100 mg/kg/day EGCG treatment. The daily disease activity index (DAI) of the mice was recorded, changes in the organizational structure of the colon were observed and the spleen index (SI) was measured. In addition, levels of interleukin (IL)-6, IL-10, IL-17 and transforming growth factor (TGF)-β1 in the plasma and hypoxia-inducible factor (HIF)-1α and signal transducer and activator of transcription (STAT) 3 protein expression in colon tissues were evaluated. Compared with the MD group, the mice in the two EGCG treatment groups exhibited decreased DAIs and SIs and an attenuation in the colonic tissue erosion. EGCG could reduce the release of IL-6 and IL-17 and regulate the mouse splenic regulatory T-cell (Treg)/T helper 17 cell (Th17) ratio, while increasing the plasma levels of IL-10 and TGF-β1 and decreasing the HIF-1α and STAT3 protein expression in the colon. The experiments confirmed that EGCG treated mice with experimental colitis by inhibiting the release of IL-6 and regulating the body Treg/Th17 balance [88].

In some embodiments, treatment of neuroinflammation associated with head injury is performed. It is widely known that one result of a head injury is inflammation. However, the concept of propagating inflammation and self-maintaining inflammation is something relatively new. In contrast to traditional TBI, in which there is one major acute insult, CTE is characterized by multiple smaller insults, and in some cases progression of pathology increases despite large periods of time during after which the damaging agent has been removed. One of the cardinal features of CTE, which initiates with the concussive or subconcussive brain injury is the activation of the microglia. The microglia cells are brain residing macrophage lineage cells whose main physiological function is the phagocytosis of debris, as well as protection of the CNS from various pathogens. In one study, immuno-histochemistry for reactive microglia (CD68 and CR3/43) was performed on human autopsy brain tissue and assessed 'blind' by quantitative image analysis. Head injury cases were compared with age matched controls, and within the traumatic brain injury group cases with diffuse traumatic axonal injury were compared with cases without diffuse traumatic axonal injury. The study found a neuroinflammatory response that develops within the first week and persists for several months after traumatic brain injury [89]. In a CTE study, the effects of repetitive head impacts (RHI) on the development of neuroinflammation and its relationship to CTE where examined. Specifically, the investigation aimed to determine the relationship between RHI exposure, neuroinflammation, and the development of hyperphosphorylated tau (pTau) pathology and dementia risk in CTE.

A cohort of 66 deceased American football athletes from the Boston University-Veteran's Affairs-Concussion Legacy Foundation Brain Bank as well as 16 non-athlete controls where utilized for the investigation. Subjects with a neurodegenerative disease other than CTE were excluded. Counts of total and activated microglia, astrocytes, and phosphorylated tau pathology were performed in the dorsolateral frontal cortex (DLF). Binary logistic and simultaneous equation regression models were used to test associations between RHI exposure, microglia, pTau pathology, and dementia. Duration of RHI exposure and the development and severity of CTE were associated with reactive microglial morphology and increased numbers of CD68 immunoreactive microglia in the DLF. A simultaneous equation regression model demonstrated that RHI exposure had a significant direct effect on CD68 cell density (p<0.0001) and pTau pathology (p<0.0001) independent of age at death. The effect of RHI on pTau pathology was partially mediated through increased CD68 positive cell density. A binary logistic regression demonstrated that a diagnosis of dementia was significantly predicted by CD68 cell density (OR=1.010, p=0.011) independent of age (OR=1.055, p=0.007), but this effect disappeared when pTau pathology was included in the model. In conclusion, RHI is associated with chronic activation of microglia, which may partially mediate the effect of RHI on the development of pTau pathology and dementia in CTE. The authors concluded that inflammatory molecules may be important diagnostic or predictive biomarkers as well as promising therapeutic targets in CTE [90].

It is known that activated microglia produce kynurenine, in part through upregulation of the enzyme indolamine 2,3-deoxygenase (IDO) [91-95]. An imbalance of neuroactive kynurenine pathway metabolites has been proposed as one mechanism behind the neuropsychiatric sequelae of certain neurological disorders. It has been hypothesized that concussed football players would have elevated plasma levels of neurotoxic kynurenine metabolites and reduced levels of neuroprotective metabolites relative to healthy football players and that altered kynurenine levels would correlate with post-concussion mood symptoms. In one study, Mood scales and plasma concentrations of kynurenine metabolites were assessed in concussed (N=18; 1.61 days post-injury) and healthy football players (N=18). A subset of football players returned at 1-week (N=14; 9.29 days) and 1-month post-concussion (N=14, 30.93 days).

Concussed athletes had significantly elevated levels of quinolinic acid (QUIN) and significantly lower ratios of kynurenic acid (KYNA) to QUIN at all time points compared with healthy athletes (p's<0.05), with no longitudinal evidence of normalization of KYNA or KYNA/QUIN. At 1-day post-injury, concussed athletes with lower levels of the putatively neuroprotective KYNA/QUIN ratio reported significantly worse depressive symptoms (p=0.04), and a trend toward worse anxiety symptoms (p=0.06), while at 1-month higher QUIN levels were associated with worse mood symptoms (p's<0.01). Finally, concussed athletes with worse concussion outcome, defined as number of days until return-to-play, had higher QUIN and lower KYNA/QUIN at 1-month post-injury (p's<0.05). The authors concluded that the results converge with existing kynurenine literature on psychiatric patients and provide the first evidence of altered peripheral levels of kynurenine metabolites following sports-related concussion [96].

Direct monitoring of brain inflammation in vivo has been reported in a pilot study in which former National Football League (NFL) players were examined by new neuroimaging techniques and clinical measures of cognitive functioning. It was hypothesized that former NFL players would show molecular and structural changes in medial temporal and parietal lobe structures as well as specific cognitive deficits, namely those of verbal learning and memory. A significant increase in binding of [(11)C]DPA-713 to the translocator protein (TSPO), a marker of brain injury and repair, in several brain regions, such as the supramarginal gyms and right amygdala, in 9 former NFL players compared to 9 age-matched, healthy controls was observed. Additionally, significant atrophy of the right hippocampus was seen. Finally, these same former players had varied performance on a test of verbal learning and memory, suggesting that these molecular and pathologic changes may play a role in cognitive decline. These results suggest that localized brain injury and repair, indicated by increased [(11)C]DPA-713 binding to TSPO, may be linked to history of NFL play. [(11)C]DPA-713 PET is a promising new tool that can be used in future study design to examine further the relationship between TSPO expression in brain injury and repair, selective regional brain atrophy, and the potential link to deficits in verbal learning and memory after NFL play [97].

Example 1

Water filled basin which was 120 cm in diameter was broken into 4 quadrants. 10 cm diameter platform placed 1 cm below water. Mice were forced to swim to find the hidden platform, starting from all four different quadrants, each day for 5 days. The time was recorded that it took the animals to find the platform. More training, faster they find it. LPS induced memory loss. Pretreatment with the product containing a) epigallocatechin-3-gallate b) thymoquinone, c) sulforaphane, and d) pterostilbene sold under the trademark QUADRAMUNE® preserved memory. Results are shown in FIG. 1.

Example 2

Figure 2:
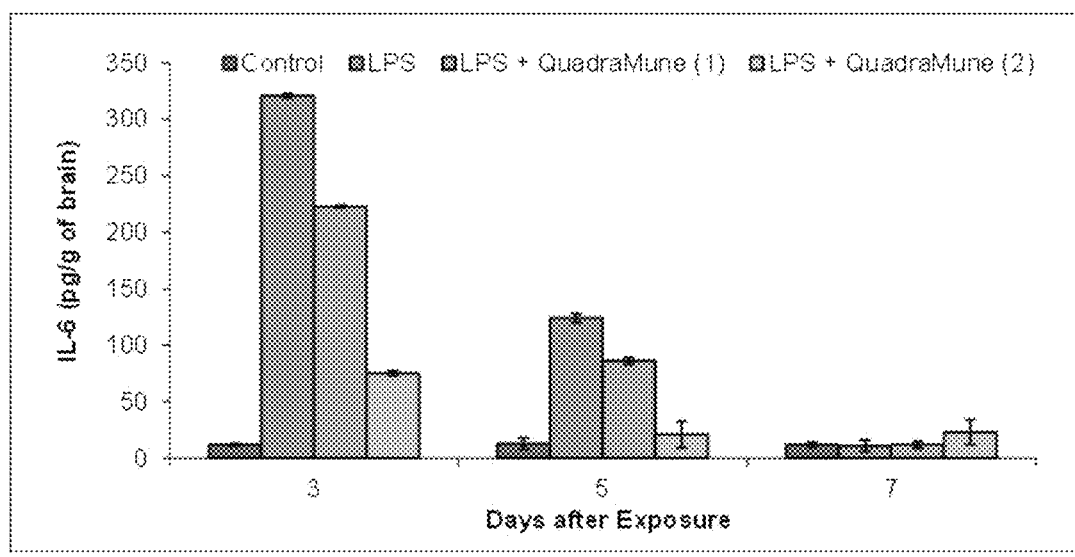
FIG. 2 is a bar graph showing IL-6 production in brain.

Mice were administered saline, LPS, LPS+the product containing a) epigallocatechin-3-gallate b) thymoquinone, c) sulforaphane, and d) pterostilbene sold under the trademark QUADRAMUNE® (1) and LPS+the product containing a) epigallocatechin-3-gallate b) thymoquinone, c) sulforaphane, and d) pterostilbene sold under the trademark QUADRAMUNE® (2). Sacrificed at indicated times. Brain tissue homogenated assessed for IL-6 cytokine production. Quantified using ELISA. Results are shown in FIG. 2.

REFERENCES

1. G McCormack D, McFadden D: A review of pterostilbene antioxidant activity and disease modification. *Oxid Med Cell Longev* 2013, 2013:575482.
2. Paul B, Masih I, Deopujari J, Charpentier C: Occurrence of resveratrol and pterostilbene in age-old darakchasava, an ayurvedic medicine from India. *J Ethnopharmacol* 1999, 68(1-3):71-76.
3. Kapetanovic I M, Muzzio M, Huang Z, Thompson T N, McCormick D L: Pharmacokinetics, oral bioavailability, and metabolic profile of resveratrol and its dimethylether analog, pterostilbene, in rats. *Cancer Chemother Pharmacol* 2011, 68(3):593-601.
4. Perecko T, Drabikova K, Rackova L, Ciz M, Podborska M, Lojek A, Harmatha J, Smidrkal J, Nosal R, Jancinova V: Molecular targets of the natural antioxidant pterostilbene: effect on protein kinase C, caspase-3 and apoptosis in human neutrophils in vitro. *Neuro Endocrinol Lett* 2010, 31 Suppl 2:84-90.
5. Stivala L A, Savio M, Carafoli F, Perucca P, Bianchi L, Maga G, Forti L, Pagnoni U M, Albini A, Prosperi E et al: Specific structural determinants are responsible for the antioxidant activity and the cell cycle effects of resveratrol. *J Biol Chem* 2001, 276(25):22586-22594.
6. Athar M, Back J H, Tang X, Kim K H, Kopelovich L, Bickers D R, Kim A L: Resveratrol: a review of preclinical studies for human cancer prevention. *Toxicol Appl Pharmacol* 2007, 224(3):274-283.
7. Bishayee A: Cancer prevention and treatment with resveratrol: from rodent studies to clinical trials. *Cancer Prev Res (Phila)* 2009, 2(5):409-418.
8. Hsu C L, Lin Y J, Ho C T, Yen G C: The inhibitory effect of pterostilbene on inflammatory responses during the interaction of 3T3-L1 adipocytes and RAW 264.7 macrophages. *J Agric Food Chem* 2013, 61(3):602-610.
9. McCormack D, McDonald D, McFadden D: Pterostilbene ameliorates tumor necrosis factor alpha-induced pancreatitis in vitro. *J Surg Res* 2012, 178(1):28-32.
10. Erasalo H, Hamalainen M, Leppanen T, Maki-Opas I, Laavola M, Haavikko R, Yli-Kauhaluoma J, Moilanen E: Natural Stilbenoids Have Anti-Inflammatory Properties in Vivo and Down-Regulate the Production of Inflammatory Mediators N O, IL6, and MCP1 Possibly in a PI3K/Akt-Dependent Manner. *J Nat Prod* 2018, 81(5):1131-1142.
11. Allijn I E, Vaessen S F, Quarles van Ufford L C, Beukelman K J, de Winther M P, Storm G, Schiffelers R M: Head-to-Head Comparison of Anti-Inflammatory Performance of Known Natural Products In Vitro. *PLoS One* 2016, 11(5):e0155325.
12. Meng X L, Yang J Y, Chen G L, Wang L H, Zhang L J, Wang S, Li J, Wu C F: Effects of resveratrol and its derivatives on lipopolysaccharide-induced microglial activation and their structure-activity relationships. *Chem Biol Interact* 2008, 174(1):51-59.
13. Zhang L, Zhou G, Song W, Tan X, Guo Y, Zhou B, Jing H, Zhao S, Chen L: Pterostilbene protects vascular endothelial cells against oxidized low-density lipoprotein-induced apoptosis in vitroand in vivo. *Apoptosis* 2012, 17(1):25-36.
14. Park S H, Jeong S O, Chung H T, Pae H O: Pterostilbene, an Active Constituent of Blueberries, Stimulates Nitric Oxide Production via Activation of Endothelial Nitric Oxide Synthase in Human Umbilical Vein Endothelial Cells. *Plant Foods Hum Nutr* 2015, 70(3):263-268.
15. Chen Z W, Miu H F, Wang H P, Wu Z N, Wang W J, Ling Y J, Xu X H, Sun H J, Jiang X: Pterostilbene protects against uraemia serum-induced endothelial cell damage via activation of Keap1/Nrf2/HO-1 signaling. *Int Urol Nephrol* 2018, 50(3):559-570.
16. Chen C, Song C, Zhang D, Yin D, Zhang R, Chen J, Dou K: Effect of resveratrol combined with atorvastatin on re-endothelialization after drug-eluting stents implantation and the underlying mechanism. *Life Sci* 2020, 245: 117349.
17. Bekpinar S, Karaca E, Yamakoglu S, Alp-Yildirim F I, Olgac V, Uydes-Dogan B S, Cibali E, Gultepe S, Uysal M: Resveratrol ameliorates the cyclosporine-induced vascular and renal impairments: possible impact of the modulation of renin-angiotensin system. *Can J Physiol Pharmacol* 2019, 97(12):1115-1123.
18. Swamy S M, Tan B K: Cytotoxic and immunopotentiating effects of ethanolic extract of *Nigella sativa* L. seeds. *J Ethnopharmacol* 2000, 70(1):1-7.
19. Salem M L, Alenzi F Q, Attia W Y: Thymoquinone, the active ingredient of *Nigella sativa* seeds, enhances survival and activity of antigen-specific CD8-positive T cells in vitro. *Br J Biomed Sci* 2011, 68(3): 131-137.
20. Majdalawieh A F, Hmaidan R, Carr R I: *Nigella sativa* modulates splenocyte proliferation, Th1/Th2 cytokine profile, macrophage function and NK anti-tumor activity. *J Ethnopharmacol* 2010, 131(2):268-275.
21. Salomi M J, Panikkar K R, Kesavan M, Donata K, Sr., Rajagopalan K: Anti-cancer activity of *Nigella sativa*. *Anc Sci Life* 1989, 8(3-4):262-266.
22. Salomi N J, Nair S C, Jayawardhanan K K, Varghese C D, Panikkar K R: Antitumour principles from *Nigella sativa* seeds. *Cancer Lett* 1992, 63(1):41-46.
23. Ait Mbarek L, Ait Mouse H, Elabbadi N, Bensalah M, Gamouh A, Aboufatima R, Benharref A, Chait A, Kamal M, Dalal A et al: Anti-tumor properties of blackseed (*Nigella sativa* L.) extracts. *Braz J Med Biot Res* 2007, 40(6):839-847.
24. Amara A A, El-Masry M H, Bogdady H H: Plant crude extracts could be the solution: extracts showing in vivo antitumorigenic activity. *Pak J Pharm Sci* 2008, 21(2): 159-171.
25. Banerjee S, Padhye S, Azmi A, Wang Z, Philip P A, Kucuk O, Sarkar F H, Mohammad R M: Review on molecular and therapeutic potential of thymoquinone in cancer. *Nutr Cancer* 2010, 62(7):938-946.

26. Khan M A, Chen H C, Tania M, Zhang D Z: Anticancer activities of *Nigella sativa* (black cumin). *Afr J Tradit Complement Altern Med* 2011, 8(5 Suppl): 226-232.
27. Woo C C, Kumar A P, Sethi G, Tan K H: Thymoquinone: potential cure for inflammatory disorders and cancer. *Biochem Pharmacol* 2012, 83(4):443-451.
28. Lei X, Lv X, Liu M, Yang Z, Ji M, Guo X, Dong W: Thymoquinone inhibits growth and augments 5-fluorouracil-induced apoptosis in gastric cancer cells both in vitro and in vivo. *Biochem Biophys Res Commun* 2012, 417 (2):864-868.
29. Linjawi S A, Khalil W K, Hassanane M M, Ahmed E S: Evaluation of the protective effect of *Nigella sativa* extract and its primary active component thymoquinone against DMBA-induced breast cancer in female rats. *Arch Med Sci* 2015, 11(1):220-229.
30. Majdalawieh A F, Fayyad M W: Recent advances on the anti-cancer properties of *Nigella sativa*, a widely used food additive. *J Ayurveda Integr Med* 2016, 7(3):173-180.
31. Majdalawieh A F, Fayyad M W, Nasrallah G K: Anti-cancer properties and mechanisms of action of thymoquinone, the major active ingredient of *Nigella sativa*. *Crit Rev Food Sci Nutr* 2017, 57(18):3911-3928.
32. Mostofa A G M, Hossain M K, Basak D, Bin Sayeed M S: Thymoquinone as a Potential Adjuvant Therapy for Cancer Treatment: Evidence from Preclinical Studies. *Front Pharmacol* 2017, 8:295.
33. Asaduzzaman Khan M, Tania M, Fu S, Fu J: Thymoquinone, as an anticancer molecule: from basic research to clinical investigation. *Oncotarget* 2017, 8(31):51907-51919.
34. Imran M, Rauf A, Khan I A, Shahbaz M, Qaisrani T B, Fatmawati S, Abu-Izneid T, Imran A, Rahman K U, Gondal T A: Thymoquinone: A novel strategy to combat cancer: A review. *Biomed Pharmacother* 2018, 106:390-402.
35. Zhang Y, Fan Y, Huang S, Wang G, Han R, Lei F, Luo A, Jing X, Zhao L, Gu S et al: Thymoquinone inhibits the metastasis of renal cell cancer cells by inducing autophagy via AMPK/mTOR signaling pathway. *Cancer Sci* 2018, 109(12):3865-3873.
36. Ulasli M, Gurses S A, Bayraktar R, Yumrutas O, Oztuzcu S, Igci M, Igci Y Z, Cakmak E A, Arslan A: The effects of *Nigella sativa* (Ns), *Anthemis hyalina* (Ah) and *Citrus sinensis* (Cs) extracts on the replication of coronavirus and the expression of TRP genes family. *Mol Biol Rep* 2014, 41(3):1703-1711.
37. Ahmad A, Husain A, Mujeeb M, Khan S A, Najmi A K, Siddique N A, Damanhouri Z A, Anwar F: A review on therapeutic potential of *Nigella sativa*: A miracle herb. *Asian Pac J Trop Biomed* 2013, 3(5):337-352.
38. Alemi M, Sabouni F, Sanjarian F, Haghbeen K, Ansari S: Anti-inflammatory effect of seeds and callus of *Nigella sativa* L. extracts on mix glial cells with regard to their thymoquinone content. *AAPS PharmSciTech* 2013, 14(1): 160-167.
39. Shuid A N, Mohamed N, Mohamed I N, Othman F, Suhaimi F, Mohd Ramli E S, Muhammad N, Soelaiman I N: *Nigella sativa*: A Potential Antiosteoporotic Agent. *Evid Based Complement Alternat Med* 2012, 2012: 696230.
40. El Mezayen R, El Gazzar M, Nicolls M R, Marecki J C, Dreskin S C, Nomiyama H: Effect of thymoquinone on cyclooxygenase expression and prostaglandin production in a mouse model of allergic airway inflammation. *Immunol Lett* 2006, 106(1): 72-81.
41. Chehl N, Chipitsyna G, Gong Q, Yeo C J, Arafat H A: Anti-inflammatory effects of the *Nigella sativa* seed extract, thymoquinone, in pancreatic cancer cells. *HPB (Oxford)* 2009, 11(5):373-381.
42. Alkharfy K M, Al-Daghri N M, Al-Attas O S, Alokail M S: The protective effect of thymoquinone against sepsis syndrome morbidity and mortality in mice. *Int Immunopharmacol* 2011, 11(2):250-254.
43. Shen G, Khor T O, Hu R, Yu S, Nair S, Ho C T, Reddy B S, Huang M T, Newmark H L, Kong A N: Chemoprevention of familial adenomatous polyposis by natural dietary compounds sulforaphane and dibenzoylmethane alone and in combination in ApcMin/+ mouse. *Cancer Res* 2007, 67(20):9937-9944.
44. Zambrano V, Bustos R, Mahn A: Insights about stabilization of sulforaphane through microencapsulation. *Heliyon* 2019, 5(11):e02951.
45. Steinkellner H, Rabot S, Freywald C, Nobis E, Scharf G, Chabicovsky M, Knasmuller S, Kassie F: Effects of cruciferous vegetables and their constituents on drug metabolizing enzymes involved in the bioactivation of DNA-reactive dietary carcinogens. *Mutat Res* 2001, 480-481:285-297.
46. Fahey J W, Zhang Y, Talalay P: Broccoli sprouts: an exceptionally rich source of inducers of enzymes that protect against chemical carcinogens. *Proc Natl Acad Sci USA* 1997, 94(19):10367-10372.
47. Solowiej E, Kasprzycka-Guttman T, Fiedor P, Rowinski W: Chemoprevention of cancerogenesis—the role of sulforaphane. *Acta Pol Pharm* 2003, 60(1):97-100.
48. Gills J J, Jeffery E H, Matusheski N V, Moon R C, Lantvit D D, Pezzuto J M: Sulforaphane prevents mouse skin tumorigenesis during the stage of promotion. *Cancer Lett* 2006, 236(1):72-79.
49. Myzak M C, Dashwood W M, Orner G A, Ho E, Dashwood R H: Sulforaphane inhibits histone deacetylase in vivo and suppresses tumorigenesis in Apc-minus mice. *FASEB J* 2006, 20(3):506-508.
50. Singh A V, Xiao D, Lew K L, Dhir R, Singh S V: Sulforaphane induces caspase-mediated apoptosis in cultured PC-3 human prostate cancer cells and retards growth of PC-3 xenografts in vivo. *Carcinogenesis* 2004, 25(1):83-90.
51. Wang L, Liu D, Ahmed T, Chung F L, Conaway C, Chiao J W: Targeting cell cycle machinery as a molecular mechanism of sulforaphane in prostate cancer prevention. *Int J Oncol* 2004, 24(1):187-192.
52. Pham N A, Jacobberger J W, Schimmer A D, Cao P, Gronda M, Hedley D W: The dietary isothiocyanate sulforaphane targets pathways of apoptosis, cell cycle arrest, and oxidative stress in human pancreatic cancer cells and inhibits tumor growth in severe combined immunodeficient mice. *Mol Cancer Ther* 2004, 3(10): 1239-1248.
53. Thejass P, Kuttan G: Antimetastatic activity of Sulforaphane. *Life Sci* 2006, 78(26):3043-3050.
54. Fimognari C, Hrelia P: Sulforaphane as a promising molecule for fighting cancer. *Mutat Res* 2007, 635(2-3): 90-104.
55. Li Y, Zhang T, Korkaya H, Liu S, Lee H F, Newman B, Yu Y, Clouthier S G, Schwartz S J, Wicha M S et al: Sulforaphane, a dietary component of broccoli/broccoli sprouts, inhibits breast cancer stem cells. *Clin Cancer Res* 2010, 16(9):2580-2590.
56. Lin W, Wu R T, Wu T, Khor T O, Wang H, Kong A N: Sulforaphane suppressed LPS-induced inflammation in 57. Ruhee R T, Ma S, Suzuki K: Sulforaphane Protects Cells against Lipopolysaccharide-Stimulated Inflammation in Murine Macrophages. *Antioxidants (Basel)* 2019, 8(12).
58. Xu X, Han M, Li T, Sun W, Wang D, Fu B, Zhou Y, Zheng X, Yang Y, Li X et al: Effective treatment of severe COVID-19 patients with tocilizumab. *Proc Natl Acad Sci USA* 2020.
59. Liu F, Li L, Xu M, Wu J, Luo D, Zhu Y, Li B, Song X, Zhou X: Prognostic value of interleukin-6, C-reactive protein, and procalcitonin in patients with COVID-19. *J Clin Virol* 2020, 127:104370.
60. Aziz M, Fatima R, Assaly R: Elevated Interleukin-6 and Severe COVID-19: A Meta-Analysis. *J Med Virol* 2020.
61. Chen X, Zhao B, Qu Y, Chen Y, Xiong J, Feng Y, Men D, Huang Q, Liu Y, Yang B et al: Detectable serum SARS-CoV-2 viral load (RNAaemia) is closely correlated with drastically elevated interleukin 6 (IL-6) level in critically ill COVID-19 patients. *Clin Infect Dis* 2020.
62. Zhang C, Wu Z, Li J W, Zhao H, Wang G Q: The cytokine release syndrome (CRS) of severe COVID-19 and Interleukin-6 receptor (IL-6R) antagonist Tocilizumab may be the key to reduce the mortality. *Int J Antimicrob Agents* 2020:105954.
63. Zhang X, Song K, Tong F, Fei M, Guo H, Lu Z, Wang J, Zheng C: First case of COVID-19 in a patient with multiple myeloma successfully treated with tocilizumab. *Blood Adv* 2020, 4(7):1307-1310.
64. McGonagle D, Sharif K, O'Regan A, Bridgewood C: The Role of Cytokines including Interleukin-6 in COVID-19 induced Pneumonia and Macrophage Activation Syndrome-Like Disease. *Autoimmun Rev* 2020:102537.
65. Luo P, Liu Y, Qiu L, Liu X, Liu D, Li J: Tocilizumab treatment in COVID-19: A single center experience. *J Med Virol* 2020.
66. Ulhaq Z S, Soraya G V: Interleukin-6 as a potential biomarker of COVID-19 progression. *Med Mal Infect* 2020.
67. Fu B, Xu X, Wei H: Why tocilizumab could be an effective treatment for severe COVID-19? *J Transl Med* 2020, 18(1):164.
68. Liu B, Li M, Zhou Z, Guan X, Xiang Y: Can we use interleukin-6 (IL-6) blockade for coronavirus disease 2019 (COVID-19)-induced cytokine release syndrome (CRS)? *J Autoimmun* 2020:102452.
69. Eren E, Tufekci K U, Isci K B, Tastan B, Genc K, Genc S: Sulforaphane Inhibits Lipopolysaccharide-Induced Inflammation, Cytotoxicity, Oxidative Stress, and miR-155 Expression and Switches to Mox Phenotype through Activating Extracellular Signal-Regulated Kinase ½-Nuclear Factor Erythroid 2-Related Factor 2/Antioxidant Response Element Pathway in Murine Microglial Cells. *Front Immunol* 2018, 9:36.
70. Ma T, Zhu D, Chen D, Zhang Q, Dong H, Wu W, Lu H, Wu G: Sulforaphane, a Natural Isothiocyanate Compound, Improves Cardiac Function and Remodeling by Inhibiting Oxidative Stress and Inflammation in a Rabbit Model of Chronic Heart Failure. *Med Sci Monit* 2018, 24:1473-1483.
71. Liu H, Zimmerman A W, Singh K, Connors S L, Diggins E, Stephenson K K, Dinkova-Kostova A T, Fahey J W: Biomarker Exploration in Human Peripheral Blood Mononuclear Cells for Monitoring Sulforaphane Treatment Responses in Autism Spectrum Disorder. *Sci Rep* 2020, 10(1):5822.
72. Lopez-Chillon M T, Carazo-Diaz C, Prieto-Merino D, Zafrilla P, Moreno D A, Villano D: Effects of long-term consumption of broccoli sprouts on inflammatory markers in overweight subjects. *Clin Nutr* 2019, 38(2):745-752.
73. Qi T, Xu F, Yan X, Li S, Li H: Sulforaphane exerts anti-inflammatory effects against lipopolysaccharide-induced acute lung injury in mice through the Nrf2/ARE pathway. *Int J Mol Med* 2016, 37(1):182-188.
74. Dashwood R H, Xu M, Hernaez J F, Hasaniya N, Youn K, Razzuk A: Cancer chemopreventive mechanisms of tea against heterocyclic amine mutagens from cooked meat. *Proc Soc Exp Biol Med* 1999, 220(4):239-243.
75. Brown M D: Green tea (*Camellia sinensis*) extract and its possible role in the prevention of cancer. *Altern Med Rev* 1999, 4(5):360-370.
76. Banerjee S, Manna S, Mukherjee S, Pal D, Panda C K, Das S: Black tea polyphenols restrict benzopyrene-induced mouse lung cancer progression through inhibition of Cox-2 and induction of caspase-3 expression. *Asian Pac J Cancer Prev* 2006, 7(4):661-666.
77. Shimizu M, Shirakami Y, Moriwaki H: Targeting receptor tyrosine kinases for chemoprevention by green tea catechin, EGCG. *Int J Mol Sci* 2008, 9(6):1034-1049.
78. Johnson J J, Bailey H H, Mukhtar H: Green tea polyphenols for prostate cancer chemoprevention: a translational perspective. *Phytomedicine* 2010, 17(1):3-13.
79. Kim J W, Amin A R, Shin D M: Chemoprevention of head and neck cancer with green tea polyphenols. *Cancer Prev Res (Phila)* 2010, 3(8):900-909.
80. Henning S M, Wang P, Heber D: Chemopreventive effects of tea in prostate cancer: green tea versus black tea. *Mol Nutr Food Res* 2011, 55(6):905-920.
81. Du G J, Zhang Z, Wen X D, Yu C, Calway T, Yuan C S, Wang C Z: Epigallocatechin Gallate (EGCG) is the most effective cancer chemopreventive polyphenol in green tea. *Nutrients* 2012, 4(11):1679-1691.
82. Henning S M, Wang P, Abgaryan N, Vicinanza R, de Oliveira D M, Zhang Y, Lee R P, Carpenter C L, Aronson W J, Heber D: Phenolic acid concentrations in plasma and urine from men consuming green or black tea and potential chemopreventive properties for colon cancer. *Mol Nutr Food Res* 2013, 57(3):483-493.
83. Schramm L: Going Green: The Role of the Green Tea Component EGCG in Chemoprevention. *J Carcinog Mutagen* 2013, 4(142):1000142.
84. Rahmani A H, Al Shabrmi F M, Allemailem K S, Aly S M, Khan M A: Implications of Green Tea and Its Constituents in the Prevention of Cancer via the Modulation of Cell Signalling Pathway. *Biomed Res Int* 2015, 2015:925640.
85. Lin Y L, Lin J K: (−)-Epigallocatechin-3-gallate blocks the induction of nitric oxide synthase by down-regulating lipopolysaccharide-induced activity of transcription factor nuclear factor-kappaB. *Mol Pharmacol* 1997, 52(3):465-472.
86. Jiang J, Mo Z C, Yin K, Zhao G J, Lv Y C, Ouyang X P, Jiang Z S, Fu Y, Tang C K: Epigallocatechin-3-gallate prevents TNF-alpha-induced NF-kappaB activation thereby upregulating ABCA1 via the Nrf2/Keap1 pathway in macrophage foam cells. *Int J Mol Med* 2012, 29(5): 946-956.
87. Aneja R, Hake P W, Burroughs T J, Denenberg A G, Wong H R, Zingarelli B: Epigallocatechin, a green tea polyphenol, attenuates myocardial ischemia reperfusion injury in rats. *Mol Med* 2004, 10(1-6):55-62.
88. Xu Z, Wei C, Zhang R U, Yao J, Zhang D, Wang L: Epigallocatechin-3-gallate-induced inhibition of interleukin-6 release and adjustment of the regulatory T/T helper 17 cell balance in the treatment of colitis in mice. Exp Ther Med 2015, 10(6):2231-2238.

89. Smith C, Gentleman S M, Leclercq P D, Murray L S, Griffin W S, Graham D I, Nicoll J A: The neuroinflammatory response in humans after traumatic brain injury. *Neuropathol Appl Neurobiol* 2013, 39(6):654-666.

90. Cherry J D, Tripodis Y, Alvarez V E, Huber B, Kiernan P T, Daneshvar D H, Mez J, Montenigro P H, Solomon T M, Alosco M L et al: Microglial neuroinflammation contributes to tau accumulation inchronic traumatic encephalopathy. *Acta Neuropathol Commun* 2016, 4(1):112.

91. Alberati-Giani D, Ricciardi-Castagnoli P, Kohler C, Cesura A M: Regulation of the kynurenine metabolic pathway by interferon-gamma in murine cloned macrophages and microglial cells. *J Neurochem* 1996, 66(3):996-1004.

92. Alberati-Giani D, Cesura A M: Expression of the kynurenine enzymes in macrophages and microglial cells: regulation by immune modulators. *Amino Acids* 1998, 14(1-3):251-255.

93. Guillemin G J, Brew B J, Noonan C E, Takikawa O, Cullen K M: Indoleamine 2,3 dioxygenase and quinolinic acid immunoreactivity in Alzheimer's disease hippocampus. *Neuropathol Appl Neurobiol* 2005, 31(4):395-404.

94. O'Farrell K, Fagan E, Connor T J, Harkin A: Inhibition of the kynurenine pathway protects against reactive microglial-associated reductions in the complexity of primary cortical neurons. *Eur J Pharmacol* 2017, 810:163-173.

95. Garrison A M, Parrott J M, Tunon A, Delgado J, Redus L, O'Connor J C: Kynurenine pathway metabolic balance influences microglia activity: Targeting kynurenine monooxygenase to dampen neuroinflammation. *Psychoneuroendocrinology* 2018, 94:1-10.

96. Singh R, Savitz J, Teague T K, Polanski D W, Mayer A R, Bellgowan P S, Meier T B: Mood symptoms correlate with kynurenine pathway metabolites following sports-related concussion. *J Neurol Neurosurg Psychiatry* 2016, 87(6):670-675.

97. Coughlin J M, Wang Y, Munro C A, Ma S, Yue C, Chen S, Airan R, Kim P K, Adams A V, Garcia C et Neuroinflammation and brain atrophy in former NFL players: An in vivo multimodal imagingpilot study. *Neurobiol Dis* 2015, 74:58-65.

The invention claimed is:

1. A method of inhibiting inflammation associated memory dysfunction comprising:
    identifying a patient suffering from inflammation associated memory dysfunction;
    administering to said patient a composition comprising the following ingredients: (a) epigallocatechin-3-gallate or a green tea extract containing epigallocatechin-3-gallate; (b) thymoquinone or a *Nigella sativa* extract containing thymoquinone; (c) sulforaphane or a broccoli extract containing sulforaphane; and (d) pterostilbene or a blueberry extract containing pterostilbene; wherein said therapeutic combination is administered at a dosage and frequency to effectively inhibit inflammation associated memory dysfunction in said patient.

2. The method of claim 1, wherein said neural inflammation is microglial activation.

3. The method of claim 2, wherein said microglial activation is upregulation of HLA II on microglia.

4. The method of claim 2, wherein said microglial activation is upregulation of IL-10 production from microglia.

5. The method of claim 2, wherein said microglial activation is upregulation of CD40.

6. The method of claim 2, wherein said microglial activation is upregulation of CD80.

7. The method of claim 2, wherein said microglial activation is upregulation of CD86.

8. The method of claim 2, wherein said microglial activation is upregulation of nitric oxide production.

9. The method of claim 1, wherein said inflammation associated memory dysfunction is caused by enhanced production of indolamine 2,3-deoxygenase metabolites.

10. The method of claim 9, wherein said indolamine 2,3-deoxygenase metabolites are quinilonic acid and kyneurinin.

* * * * *